(12) United States Patent
Brahm (10) Patent No.: US 9,770,472 B1
(45) Date of Patent: Sep. 26, 2017

(54) ORGAN JACKET AND METHODS OF USE

(71) Applicant: BioDlogics, LLC, Cordova, TN (US)

(72) Inventor: Timothy B. Brahm, Germantown, TN (US)

(73) Assignee: Brahm Holdings, LLC, Germantown, TN (US)

( * ) Notice: Subject to any disclaimer, the term of this patent is extended or adjusted under 35 U.S.C. 154(b) by 9 days.

(21) Appl. No.: 14/196,148

(22) Filed: Mar. 4, 2014

Related U.S. Application Data (60) Provisional application No. 61/774,861, filed on Mar. 8, 2013.

(51) Int. Cl.
*A61K 35/50* (2015.01)

(52) U.S. Cl.
CPC .................... *A61K 35/50* (2013.01)

(58) Field of Classification Search
None
See application file for complete search history.

(56) References Cited

U.S. PATENT DOCUMENTS

| | | | |
|---|---|---|---|
| 4,120,649 A | 10/1978 | Schechter | |
| 4,361,552 A | 11/1982 | Baur, Jr. | |
| 4,674,488 A | 6/1987 | Campbell | |
| 4,894,063 A | 1/1990 | Nashef | |
| 5,607,590 A | 3/1997 | Shimizu | |
| 5,618,312 A | 4/1997 | Yui et al. | |
| 6,152,142 A * | 11/2000 | Tseng | A01N 1/02 128/898 |
| 6,254,637 B1 | 7/2001 | Lee | |
| 6,326,019 B1 | 12/2001 | Tseng | |
| 6,599,526 B2 | 7/2003 | Dimitrijevich | |
| 9,186,382 B2 * | 11/2015 | Daniel | A61K 35/50 |
| 2001/0053839 A1 | 12/2001 | Noishiki | |
| 2003/0187515 A1 | 10/2003 | Hariri | |
| 2003/0225355 A1 | 12/2003 | Butler | |
| 2004/0048796 A1 | 3/2004 | Hariri | |
| 2007/0020225 A1 | 1/2007 | Abramson et al. | |
| 2007/0031471 A1 | 2/2007 | Peyman | |
| 2007/0038298 A1 | 2/2007 | Sulner | |
| 2008/0044848 A1 | 2/2008 | Heidaran | |
| 2008/0046095 A1 | 2/2008 | Daniel | |
| 2008/0131522 A1 | 6/2008 | Liu | |
| 2008/0181935 A1 | 7/2008 | Bhatia et al. | |
| 2008/0193554 A1 | 8/2008 | Dua | |
| 2008/0274184 A1 | 11/2008 | Hunt | |
| 2009/0208551 A1 | 8/2009 | Kim | |
| 2010/0104539 A1 | 4/2010 | Spencer | |
| 2010/0106233 A1 | 4/2010 | Deeken | |
| 2010/0292717 A1 | 11/2010 | Petter-Puchner et al. | |
| 2011/0129520 A1 | 6/2011 | Bogdansky | |
| 2011/0189301 A1 | 8/2011 | Yang | |
| 2011/0206776 A1 * | 8/2011 | Tom | A01N 1/0221 424/583 |
| 2012/0009644 A1 | 1/2012 | Goldstein | |
| 2012/0009679 A1 | 1/2012 | Walsh | |
| 2012/0078378 A1 | 3/2012 | Spencer | |
| 2012/0083900 A1 | 4/2012 | Wilkins | |
| 2013/0209524 A1 * | 8/2013 | Young | A61K 35/50 424/400 |

FOREIGN PATENT DOCUMENTS

| | | |
|---|---|---|
| EP | 0 669 138 A2 | 8/1995 |
| EP | 0781564 A2 | 7/1997 |
| WO | 2009044408 A1 | 4/2009 |
| WO | WO 2011/002926 | 1/2011 |
| WO | 2012003377 A2 | 1/2012 |
| WO | 2012112417 A2 | 8/2012 |
| WO | 2012112441 A1 | 8/2012 |

* cited by examiner

*Primary Examiner* — Allison Fox
(74) *Attorney, Agent, or Firm* — Brinks Gilson & Lione (57) ABSTRACT

An organ jacket fabricated from human birth tissue comprising at least one cross-linked amniotic membrane, or at least one cross-linked chorionic membrane, or at least one amniotic membrane, or at least one chorionic membrane, or any combination thereof. Methods of processing a membrane to form an organ jacket and methods of preventing graft rejection in solid organ transplantation and methods of reducing the incidence of acute and chronic rejection episodes after solid organ transplantation are also provided.

6 Claims, 3 Drawing Sheets

ORGAN JACKET AND METHODS OF USE

CROSS-REFERENCE TO RELATED APPLICATIONS

This application claims priority to U.S. Provisional Patent Application No. 61/774,861 filed Mar. 8, 2013, the content of which is incorporated herein in its entirety.

FIELD OF THE INVENTION

The present invention is directed to an organ jacket composed of aseptically recovered human birth tissue, as well as methods of processing the same to prepare an organ jacket and methods of using the same.

BACKGROUND OF THE INVENTION

Organ transplantation is often the only treatment for end stage organ failure, such as liver and heart failure. Surgical replacement of a diseased organ by transplantation with a normal organ obtained from a donor can be a life-saving procedure. Unfortunately, normal bodily immune defense mechanisms recognize such solid organ transplants as foreign and attack them, resulting in graft failure and rejection. Transplantation of several organs, including kidney, liver, heart, and lungs has been achieved with varying degrees of success by employing immunosuppressive drugs to interfere with immune-mediated graft rejection. Unfortunately, there is no one single immunosuppressive agent or technique which is useful in all settings involving organ transplantation, and all of the agents currently available have serious drawbacks and deleterious side effects. The usefulness of many of the agents is limited by their toxicity. In some cases, this associated toxicity may actually hinder the normal functioning of the transplant itself. Additionally, the use of such immunosuppressive agents weakens the immune system of the recipient, often making them highly vulnerable to infections.

Despite significant advances in the understanding of tissue typing (series of diagnostic tests to determine the molecular compatibility of donor and recipient) and immunosuppression therapies since the first solid organ transplant over 60 years ago, acute rejection remains a serious clinical problem only partially controlled by current immunosuppressive drugs (e.g., cyclosporine, monoclonal antibodies). In the absence of successful therapies, rejection will lead to graft failure, which, in turn, leads to recipient death or reinstitution of other procedures (e.g., dialysis for kidney patients). Thus, there remains a need in the art for a safe, effective means for preventing and/or reducing the incidence of graft rejection of solid organ transplants using a human birth tissue construct.

SUMMARY OF THE INVENTION

The present invention is generally directed to an organ jacket and processes for producing the organ jacket. The organ jacket of the present invention has unique properties that prevent or reduce the incidence of acute and chronic organ rejection episodes following solid organ transplantation. Additionally, the organ jacket acts as a protective outer covering for a transplanted solid organ by preventing clot formation and fibrous scar formation (adhesions), as well as reducing pain and inflammation after application on or around an organ.

According to one aspect, an organ jacket is provided that includes at least one cross-linked amniotic membrane, or at least one cross-linked chorionic membrane, or at least one amniotic membrane, or at least one chorionic membrane, or a combination thereof. The cross-linked membrane(s) is/are treated with a cross-linking solution comprising from about 0.05% to about 3% glutaraldehyde. The membrane(s) is/are treated with at least one alcohol composition followed by terminal sterilization to form an organ jacket. The alcohol composition comprises an ethanol composition. In a preferred embodiment, the ethanol composition comprises from about 90% to about 100% ethanol. Terminal sterilization is carried out via gamma irradiation or electron beam irradiation.

According to another aspect, a method of preparing a membrane for an organ jacket is provided. The method includes the steps of:

(a) obtaining amniotic membrane, chorionic membrane, or both amniotic and chorionic membrane from a seronegative, healthy human via Cesarean section or vaginal delivery;

(b) immersing the membrane in a basin containing a sterile saline solution;

(c) agitating the basin to liberate excess blood and fluids from the membrane;

(d) rinsing the membrane with a sterile saline solution;

(e) optionally, covering the membrane with a substrate on both the fetal membrane side and the maternal membrane side;

(f) optionally, immersing the membrane in a preservative solution for a period of up to about 20 minutes, wherein the preservative solution comprises from about 0.05% to about 3% glutaraldehyde, an alcohol composition or a combination thereof;

(g) optionally, rinsing the membrane with a sterile saline solution;

(h) optionally, soaking the membrane in a sterile saline solution;

(i) immersing the membrane in an alcohol composition;

(j) optionally, removing the optional substrate from both the fetal membrane side and the maternal membrane side;

(k) spreading the membrane on a flat, dry and sterile surface;

(l) allowing the membrane to air dry completely at ambient temperature;

(m) cutting the membrane to a predetermined size; and (n) optionally, placing the fetal side of the membrane directly onto, a pre-cut substrate to form an organ jacket or a portion thereof.

The method of preparing a membrane for an organ jacket may further include the step of fastening or fixing the membrane to one or more membranes as provided herein to form an organ jacket. In one embodiment, the membranes are fastened or fixed together with a composition or device including: tissue glue or tissue adhesive, fibrin glue, fibrinogen glue, hydrogel tissue glue, chondroitin sulfate aldehyde, sutures or any combination thereof. In another embodiment, the membranes are fastened or fixed together using vacuum lamination techniques.

The method of preparing a membrane for an organ jacket may further include the steps of packaging the organ jacket in a dry state or wet state and terminally sterilizing the packaged organ jacket using irradiation. According to one embodiment, the method may further include the step of removing the chorionic membrane via blunt dissection and discarding the chorionic membrane. According to another embodiment, the method may further include the step of placing the membrane in sterile saline solution for a period of up to about five days between steps (a) and (b). In such an embodiment, the sterile saline solution includes from about 0.9% to about 20% NaCl. According to one embodiment, the sterile saline solution in step (b) may include from about 0.9% to about 20% NaCl. According to one embodiment, the sterile saline solution in steps (d) and (g) may also include from about 0.9% to about 20% NaCl. According to one embodiment, the rinse steps (d) and (g) are conducted for a maximum time period of five minutes. According to one embodiment, the sterile saline solution in step (h) comprises from about 0.9% to about 20% NaCl, and the soak in step (h) is conducted for a maximum period of about 35 minutes. According to one embodiment, the preservative solution comprises 0.1% glutaraldehyde. According to one embodiment, the alcohol composition in steps (f) and (i) comprises an ethanol composition. According to a preferred embodiment, the alcohol composition in steps (f) and (i) each include from about 90% to about 100% ethanol. According to another embodiment, the alcohol composition in steps (f) and (i) comprises 95.5% ethanol. According to another embodiment, the alcohol composition in steps (f) and (i) comprises 100% ethanol.

According to one embodiment, the method further includes the step of treating the membrane with an oxidizer between steps (a) and (b). According to one embodiment, the oxidizer is hydrogen peroxide and the step of treating the membrane further includes the steps of:

(a) rinsing the membrane with about 120 ml of sterile isotonic solution per gram of membrane for a time period of up to about ten minutes;

(b) treating the membrane with about 60 ml of hydrogen peroxide per gram of membrane for a time period of up to about ten minutes; and (c) rinsing the membrane with about 120 ml of sterile isotonic solution per gram of membrane for a time period of up to about ten minutes.

According to another aspect, an organ jacket is provided that is produced by the aforementioned method. According to one embodiment, the ethanol residual levels determined by gas chromatography are not detected at the corresponding minimum report limit. According to one embodiment, the glutaraldehyde residual levels determined by gas chromatography are not detected at the corresponding minimum reporting limit.

According to another aspect, a method of preventing graft rejection in a recipient of a transplanted solid organ is provided. The method includes the steps of providing an organ jacket as provided herein and applying the organ jacket to an external surface of the solid organ immediately before transplant into the recipient. According to one embodiment, the solid organ is a heart, lung, liver, kidney, pancreas, intestine, endocrine gland or stomach.

According to another aspect, a method of reducing the incidence of acute and chronic rejection episodes in a recipient following a sold organ transplant is provided. The method includes the steps of providing an organ jacket as provided herein and applying the organ jacket to an external surface of the solid organ immediately before transplant into the recipient. According to one embodiment, the solid organ is a heart, lung, liver, kidney, pancreas, intestine, endocrine gland or stomach.

According to another aspect, a kit for use by a medical professional is provided. According to one embodiment, the kit includes one or more packaged and sterilized organ jackets as provided herein. The kit may further include at least one set of instructions.

DETAILED DESCRIPTION OF THE INVENTION

The present disclosure will now be described more fully hereinafter with reference to exemplary embodiments thereof. These exemplary embodiments are described so that this disclosure will be thorough and complete, and will fully convey the scope of the disclosure to those skilled in the art. Indeed, the present disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise. As used in the specification, and in the appended claims, the words "optional" or "optionally" mean that the subsequently described event or circumstance can or cannot occur. For example, the phrase "optionally soaking the membrane" means that the soaking step may or may not be performed.

As used herein, the term "human birth tissue" includes, but is not limited to, elements of the placental organ such as, for example, the placental globe, umbilical cord, associated membranes (chorionic membrane and amniotic membrane), and other placental gelatins, fluids, cells and extracellular material obtained from a seronegative, healthy human.

As used herein, and in the appended claims, the term "jacket" refers to a sheath, encasement, wrap, envelope, integument or other material embodiment suitable as a protective outer covering for an organ subjected to transplantation.

As used herein, and in the appended claims, the term "solid organ" means a heart, lung, liver, kidney, pancreas, intestine, endocrine gland or stomach.

The present invention generally relates to the use of at least one cross-linked amniotic membrane, or at least one cross-linked chorionic membrane, or at least one amniotic membrane, or at least one chorionic membrane, or a combination thereof to form an organ jacket. The organ jacket of the present invention has unique properties that prevent or reduce the incidence of acute and chronic organ rejection episodes following solid organ transplantation. In a preferred embodiment, the organ jacket acts as a protective outer covering for a transplanted solid organ by preventing clot formation and fibrous scar formation (adhesions), as well as reducing pain and inflammation after application on or around an organ.

In one aspect of the present invention, the organ jacket is a sterile, biocompatible structure that may be applied onto or around the external surface of a solid organ immediately before transplant into a recipient. The human birth tissue material giving rise to the organ jacket provides handling characteristics useful for placement and implantation of the organ jacket onto or around a solid organ. For example, the organ jacket is flexible and readily conforms to multiplanar shapes (e.g., can conform to the geometry of the organ). In certain embodiments, the organ jacket is fully resorbed by the body after placement. In other embodiments, the organ jacket remains intact on or around the solid organ. The organ jacket may be utilized in conjunction with a variety of solid organ transplantations, including, but not limited to, heart, lung, liver, kidney, pancreas, intestine, endocrine gland or stomach.

Cross-linked and non-cross-linked amniotic and chorionic membranes may be utilized alone or in various combinations or layers to form the organ jacket. The present disclosure provides methods of preparing an organ jacket that includes at least one cross-linked amniotic membrane, or at least one cross-linked chorionic membrane, or at least one amniotic membrane, or at least one chorionic membrane, or a combination thereof. Thus, the term "membrane" refers to a cross-linked amniotic membrane, a cross-linked chorionic membrane, an amniotic membrane, a chorionic membrane or any combination thereof.

According to one embodiment, the membrane(s) is/are cross-linked by treating the membrane(s) with a glutaraldehyde composition. The glutaraldehyde composition includes glutaraldehyde typically in an amount of from about 0.05% to about 3%. According to another embodiment, the membrane(s) is/are not cross-linked.

According to one embodiment, the membrane(s) is/are treated with at least one alcohol composition followed by terminal sterilization. According to an alternative embodiment, the membrane(s) is/are treated with at least two alcohol compositions. In one aspect, the alcohol composition comprises an ethanol composition. In a preferred embodiment, the ethanol composition(s) comprises from about 90% to about 100% ethanol. Terminal sterilization is carried out via gamma irradiation or electron beam irradiation.

In certain embodiments, the organ jacket is formed as a solid construct and may be of various physical sizes, thicknesses, and shapes. According to such an embodiment, the organ jacket is preferably of sufficient size and shape to be applied onto or around a solid organ. The organ jacket thickness may vary depending on the membrane composition(s), the number of membrane layers, and the type of solid organ being encased. In certain embodiments, the organ jacket readily conforms to multiplanar shapes. In a preferred embodiment, the invention is custom-manufactured to encase or "jacket" the general dimensions of a particular organ of average size (e.g., adult liver or kidney). The size of the organ jacket may be adjusted to a desired size and shape at the time of implantation by a medical professional using any method known in the art (e.g., trimming and suturing). In a preferred embodiment, the organ jacket is manufactured to not only envelop the solid organ, but also to provide appropriate opening(s) for the organ's vasculature to exit the organ jacket.

In a preferred embodiment, the organ jacket is composed of a two membrane layers. According to one embodiment, the first (inner) layer includes at least one amniotic membrane, or at least one chorionic membrane, or at least one amniotic membrane and at least one chorionic membrane that is/are not cross-linked. The membrane(s) is/are treated with one or two alcohol compositions as described herein. The first layer aids in placement of the organ jacket and aids in reducing inflammation and blood clots. The second (outer) layer includes at least one cross-linked amniotic membrane, or at least one cross-linked chorionic membrane, or at least one cross-linked amniotic membrane and at least one cross-linked chorionic membrane, which may or may not be treated with an alcohol composition. The second layer is non-immunogenic and non-thrombogenic. The second layer also aids in the prevention of adhesion formation. The first and second layer are fastened or fixed together with a composition or device, including, but not limited to, tissue glue or tissue adhesive, fibrin glue, fibrinogen glue, hydrogel tissue glue, chondroitin sulfate aldehyde, sutures or any combination thereof. In another aspect, the two membranes are fastened or fixed together using vacuum lamination techniques known to those skilled in the art. Both the first (inner) layer and second (outer) layer make up an organ jacket with optimal anti-rejection characteristics.

To obtain the human birth tissue material needed to prepare an organ jacket, potential human birth tissue donors providing informed consent are pre-screened during an examination of pre-natal medical records and blood test results. A comprehensive medical history and behavior risk assessment is obtained from the donor prior to donation incorporating U.S. Public Health Service guidelines. Discussions with the physician(s) and/or the donor mother are conducted to identify circumstances that may lead to the exclusion of the donor or donated tissue. Additionally, a physical exam is performed on the donor to determine whether there is evidence of high risk behavior or infection and to determine the overall general health of the donor.

Infectious disease testing of donor blood specimens is performed for each tissue donor on a specimen collected at the time of donation or within seven days prior to or after donation. Exemplary infectious disease testing includes, but is not limited to, antibodies to the human immunodeficiency virus, type 1 and type 2 (anti-HIV-1 and anti-HIV-2); nucleic acid test (NAT) for HIV-1; hepatitis B surface antigen (HBsAg); total antibodies to hepatitis B core antigen (anti-HBc-total, meaning IgG and IgM); antibodies to the hepatitis C virus (anti-HCV); NAT for HCV; antibodies to human T-lymphotropic virus type I and type II (anti-HTLV-I and anti-HTLV-II); and syphilis (a non-treponemal or treponemal-specific assay may be performed).

Human birth tissue is preferably recovered from a full-term aseptic Cesarean delivery of a newborn. Alternatively, human birth tissue is recovered from a full-term vaginal delivery of a newborn. The placental organ, including the placental globe, umbilical cord, associated membranes (chorionic membrane and amniotic membrane), and other placental gelatins, fluids, cells and extracellular matrix can be recovered from a seronegative, healthy human after the newborn is removed. The placental globe, umbilical cord, and other placental gelatins, fluids, cells and extracellular matrix can be removed and discarded.

The membrane giving rise to the organ jacket as described herein may be produced by processing human birth tissue according to the steps provided herein. Processing does not change the physical properties of the resulting membrane so as to yield the membrane tissue unacceptable for clinical use. Instruments, solutions, and supplies coming into contact with tissue during the processing of the placental tissue are sterile. All surfaces coming in contact with tissue intended for transplant are either sterile or draped using aseptic technique.

Throughout processing, the orientation of a particular membrane may be identified to ensure that in use a particular side of the membrane is applied at a specific site on or around an organ. Either the fetal side or the maternal side of the membrane may be used depending upon the specific use or procedure that is being performed.

Figure 1:
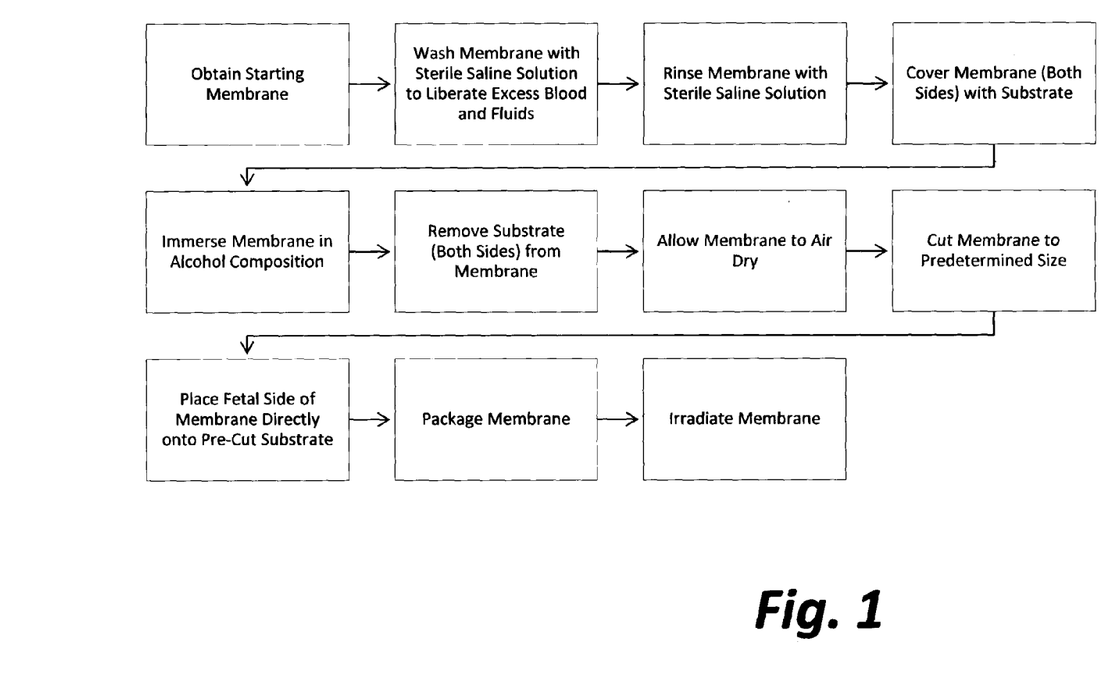
FIG. 1 illustrates a method of preparing an organ jacket or a portion thereof according to one embodiment.
Figure 2:
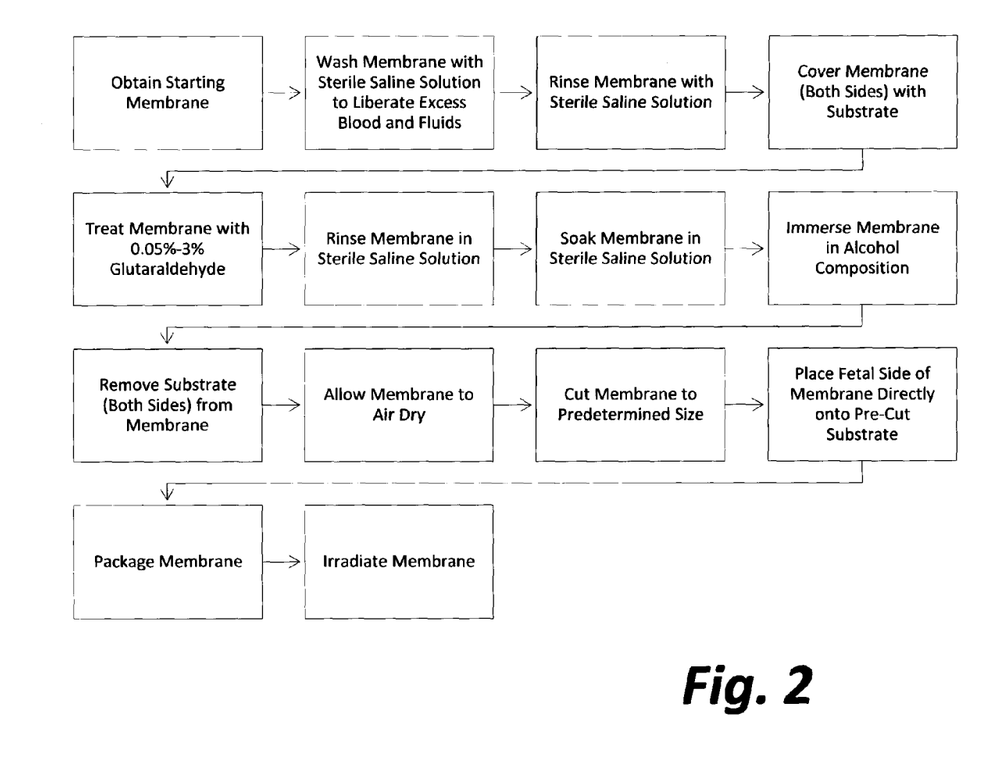
FIG. 2 illustrates a method of preparing an organ jacket or a portion thereof according to one embodiment.
Figure 3:
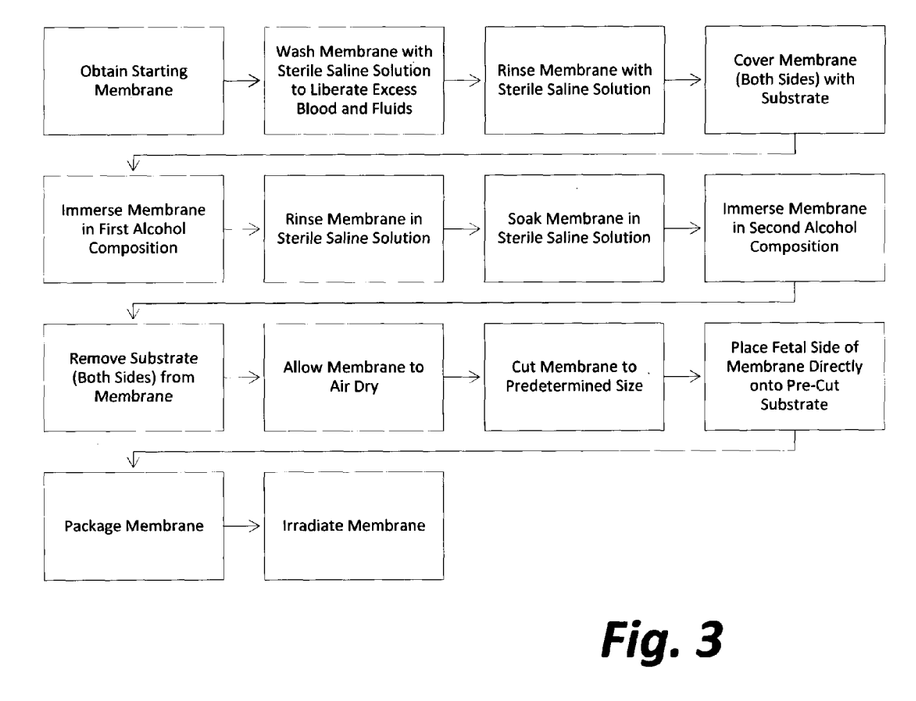
FIG. 3 illustrates a method of preparing an organ jacket or a portion thereof according to one embodiment.

According to the embodiment as illustrated in FIG. 1, FIG. 2 or FIG. 3, the organ jacket is prepared by first obtaining amniotic membrane, chorionic membrane, or both amniotic and chorionic membrane from a seronegative, healthy human via cesarean section or vaginal delivery as described herein. In particular embodiments where only the amniotic membrane is selected for further processing, the chorionic membrane can be removed by blunt dissection. For example, the chorionic membrane may be removed by applying finger pressure and sliding it off of the amniotic membrane using as little pressure as possible to avoid tearing of the amnion. The chorionic membrane and any excess tissue can be discarded.

The recovered amniotic membrane, chorionic membrane, or both amniotic and chorionic membrane may be initially stored in a sterile saline solution at a temperature between about 1° C. to about 10° C. for a period of up to about 120 hours prior to further processing. According to one embodiment, the sterile saline solution comprises from about 0.9% to about 20% NaCl, preferably 15% NaCl.

Optionally, the membrane may be treated with an oxidizer. In one embodiment, the oxidizer is hydrogen peroxide, which is also used as a sterilant and to enhance the solubilization of lipids. Such a treatment process includes the steps of:

(a) rinsing the membrane with 120 ml of sterile isotonic solution per gram of membrane for a period of up to about ten minutes;

(b) treating the membrane with 60 ml of hydrogen peroxide per gram of membrane for a period of up to about ten minutes; and (c) rinsing the membrane with 120 ml of sterile isotonic solution per gram of membrane for a period of up to about ten minutes.

The membrane is then immersed in a basin containing a sterile saline solution. According to one embodiment, the sterile saline solution includes typically from about 0.9% to about 20% NaCl.

Excess blood and fluids may be liberated from the membrane by gently stirring or swirling the fluid in a circular motion in the basin or by placing the basin on a shaker. The membrane can then be rinsed with a sterile saline solution. In one embodiment, the sterile saline solution includes NaCl in a concentration range of about 0.9% to about 20%. In one embodiment, the membrane may be rinsed in bowls or trays of sufficient size to allow the membrane to be spread out to improve the rinse coverage. Sufficient saline solution is utilized to ensure that the membrane is completely immersed. The saline is then decanted into a discard basin.

Multiple saline rinse cycles may be performed. In one embodiment, the membrane is rinsed for two or more separate rinse cycles, with each rinse cycle lasting for a maximum of five minutes. The membrane is optionally covered with a substrate on both the fetal membrane side and the maternal membrane side. Appropriate substrates include, but are not limited to, a sterile mesh or polymer mesh of adequate size and shape for covering each side of the membrane.

According to the embodiment as illustrated in FIG. 2, the membrane is then optionally immersed in a preservative solution for a period of time of typically up to about twenty minutes. The preservative solution includes typically from about 0.05% to about 3% glutaraldehyde and, preferably, about 0.1% glutaraldehyde. The membrane may then be optionally stirred or swirled at a temperature of typically about 22° C. (±1-5° C.). When present, glutaraldehyde leads to collagen cross-linking, which, in turn, leads to a significant increase in the biomechanical strength of the membrane. Additionally, the handling characteristics of the membrane are improved after glutaraldehyde treatment because the membrane is more rigid and does not fold over onto itself. Glutaraldehyde cross-linking also prohibits fast resorption of the membrane by the body after implantation. The glutaraldehyde treatment is preferably performed in a bowl or tray of sufficient size to allow the membrane to spread out in order to maximize exposure of the tissue to the glutaraldehyde solution. Sufficient glutaraldehyde solution should be used to immerse the membrane in the solution. Typically, a minimum of about 400 ml of glutaraldehyde solution is used.

According to the alternative embodiment as illustrated in FIG. 3, the preservative solution may optionally include from about 90% to about 100% ethanol (i.e., in the absence of glutaraldehyde (see FIG. 3—referred to as "first alcohol composition")). In certain embodiments, the alcohol composition includes about 95.5% ethanol. In other embodiments, the alcohol composition includes about 100% ethanol. An organ jacket produced according to the embodiment of FIG. 3 will be resorbed more quickly by the body (as opposed to glutaraldehyde treatment followed by alcohol treatment).

As illustrated in the embodiments of FIGS. 2 and 3, the membrane is then optionally rinsed with a sterile saline solution. Alternatively, the membrane is rinsed multiple times with a sterile saline solution. According to one embodiment, the sterile saline solution includes typically from about 0.9% to about 20% of NaCl. The membrane can then be optionally soaked in a sterile saline solution. According to one embodiment, the sterile saline solution includes typically from about 0.9% to about 20% of NaCl. According to one embodiment, soaking is conducted for a maximum period of about 35 minutes.

As illustrated in each of the embodiments of FIGS. 1, 2, and 3, the membrane is then immersed in an alcohol composition. The alcohol composition includes about 90% to about 100% ethanol. In certain embodiments, the alcohol composition includes about 95.5% ethanol. In other embodiments, the alcohol composition includes about 100% ethanol. Treatment of the membrane within a particular alcohol concentration range at this step in the process has yielded unexpected results related to the handling characteristics. One of ordinary skill in the art appreciates the difficulty of handling and manipulating amniotic and chorionic tissue during manipulation and application. Specifically, existing amniotic and chorionic grafts are difficult to place over or around a specific site, particularly because these grafts fold back over on themselves ("wrinkling"), rendering proper placement and positioning very challenging. When treated with the aforementioned alcohol composition, the resulting organ jacket experiences further cross-linking which aids in the handling characteristics of the organ jacket. The alcohol-treated membrane does not "wrinkle" and allows for ease of application to a specific site. Furthermore, the alcohol treatment is multi-functional, providing a means of sterilization, preservation, and chemical dehydration for the graft, in addition to serving as a radioprotectant for the construct prior to terminal irradiation.

The optional substrate can then be removed from both the fetal membrane side and the maternal membrane side. The membrane can be spread on a flat, dry and sterile surface and allowed to air dry completely at ambient temperature. The membrane can then be cut to the desired size and optionally covered with a substrate to form a membrane for an organ jacket or a portion thereof. In certain embodiments, the membrane can be cut into particular shapes of any desired size by a rotary type cutting tool. A grooved or similarly indicated cutting board may be used to aid in cutting a straight and correctly sized membrane. In another embodiment, the membrane is cut by free hand using a scalpel and ruler to achieve the desired size. Optionally, the fetal side of the membrane can then be placed directly onto a pre-cut substrate to form a membrane for an organ jacket or a portion thereof. Suitable substrates include, for example, a gauze or synthetic mesh.

The invention further provides an organ jacket comprising one or more membranes prepared by the methods described herein. In a preferred embodiment, multiple membranes are fastened or fixed together with a composition or device, including, but not limited to, tissue glue or tissue adhesive, fibrin glue, fibrinogen glue, hydrogel tissue glue, chondroitin sulfate aldehyde, sutures or any combination thereof. In another aspect, multiple membranes are fastened or fixed together using vacuum lamination techniques known to those skilled in the art.

In certain embodiments, the organ jacket is packaged in a dry state. In other embodiments, the organ jacket is packaged in a wet state, including, but not limited to, sterile water, crystalloids, ethanol, or another sterilizing, preserving or storage agent. The packaging and optional substrate as disclosed herein can facilitate the handling of the organ jacket, namely maintaining and identifying the orientation of the fetal and maternal side of the organ jacket for the user. The packaging may also promote storage of the organ jacket.

The packaged organ jacket can be terminally sterilized using irradiation. In one embodiment, an electron beam irradiation is applied in an amount up to about 45 kGy. The sterilized organ jacket may be stored for up to typically about two years from the date of processing. In one embodiment, the organ jacket may be stored under proper conditions for as much as about five years following processing. The sterilized organ jacket may be stored in any container suitable for long-term storage. Preferably, the sterilized organ jacket is stored in a sterile double peel-pouch package.

If desired, the membrane(s) of the organ jacket may be treated to provide for the delivery of a variety of antibiotics, anti-inflammatory agents, growth factors and/or other specialized proteins or small molecules that assist in the healing cascade after placement. In addition, the membrane may be combined with a substrate (sterile gauze, sterile polymer material or other tissue or biomaterial) to increase the strength of the organ jacket.

A method of preventing graft rejection in a recipient of a transplanted solid organ is also provided. The method includes the steps of providing an organ jacket as provided herein and applying the organ jacket to the external surface of a solid organ immediately before the organ is transplanted into the recipient. Exemplary solid organs include, but are not limited to, heart, lung, liver, kidney, pancreas, intestine, endocrine gland or stomach. The invention further provides for the size of the organ jacket to be adjusted to a desired size and shape at the time of implantation by a medical professional using any method known in the art (e.g., trimming and suturing). In a preferred embodiment, the organ jacket is manufactured to not only envelop the solid organ, but also to provide appropriate opening(s) for the organ's vasculature to exit the organ jacket.

A method of reducing the incidence of acute or chronic rejection episodes in a recipient following a solid organ transplant is also provided. The method includes the steps of providing an organ jacket as provided herein and applying the organ jacket to the external surface of a solid organ immediately before the organ is transplanted into a recipient. Exemplary solid organs include, but are not limited to heart, lung, liver, kidney, pancreas, intestine, endocrine gland or stomach. The invention further provides for the size of the organ jacket to be adjusted to a desired size and shape at the time of implantation by a medical professional using any method known in the art (e.g., trimming and suturing). In a preferred embodiment, the organ jacket is manufactured to not only envelop the solid organ, but also to provide appropriate opening(s) for the organ's vasculature to exit the organ jacket.

In certain embodiments, no sutures are required for the organ jacket to remain in place onto or around a solid organ. If desired, the organ jacket may be utilized with at least one composition or device for delivering, fastening or fixing the organ jacket on or around a specific site of a solid organ. Exemplary compositions include, but are not limited to, tissue glue or tissue adhesive, fibrin glue, fibrinogen glue, hydrogel tissue glue, chondroitin sulfate aldehyde, or natural proteins. Exemplary devices include, but are not limited to, sutures or forceps.

A kit for use by a medical transplant professional is also provided. According to one embodiment, the kit includes one or more packaged and sterilized organ jackets as provided herein and at least one set of instructions. The kit may further include at least one composition or device for delivering, fastening or fixing the organ jacket in place onto or around a solid organ. The kit may further include a container adapted to accommodate the aforementioned components while preserving the organ jacket as per applicable Food and Drug Administration guidelines.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

Having generally described the present invention, a further understanding can be obtained by reference to the examples provided herein for purposes of illustration only and are not intended to be limiting.

EXAMPLE 1

Representative samples of final product from four production lots #1, #2, #3 and #4 manufactured according to the methods of FIG. 2 were tested for residual glutaraldehyde and residual ethanol by gas chromatography, analytical methods EPA 8015M, CAS No. 111-30-8 and EPA 8260B, CAS No. 64-17-5, respectively. Samples were sent to Nelson Laboratories, Inc., 6280 South Redwood Road Salt Lake City, Utah 84123, a GLP qualified microbiology laboratory registered with the FDA and third-party accredited to ISO 17025 standards. The results are summarized in Table 1 and Table 2 below.

Samples from four production lots #1, #2, #3 and #4 were tested for residual glutaraldehyde by gas chromatography, analytical method EPA 8015M, CAS No. 111-30-8 as follows:

Three representative samples of final product (2 cm×2 cm each) from production lot #1 included amniotic membranes that had been treated with a 0.1% glutaraldehyde composition for a period of 15 minutes and had been immersed in an alcohol composition comprising 95.5% ethanol for a period of 24 hours.

Zero headspace extraction was performed with double deionized water as the vehicle extractant. Extraction vessels were tumbled during the entire extraction process. For production lot #1, the three samples were pooled, and a test article was extracted with a weight of 0.046 g and fluid amount of 100 ml. The starting extraction temperature was 22° C. and the ending extraction temperature was 23° C. The extraction lasted twenty-four hours.

All sample extract solutions were observed to be clear and free of particulates. At the end of the extraction period, all test articles were observed to be intact with no observable degradation. Extracts were maintained at room temperature and were not filtered prior to analysis. The vehicle solution was analyzed by gas chromatography for glutaraldehyde determination. Control blanks contained no compounds of interest at the reported detection limits. Low level calibration standards were analyzed at the detection levels, and standard percent recoveries were within acceptable method limits. No analytical interferences were observed. All instrument calibration results were within method requirements through all portions of the analysis.

No glutaraldehyde was detected at the reported detection limit (1.0 mg/L) for production lot #1.

One sample of final product (4 cm×4 cm) from production lot #2 included an amniotic membrane that had been treated with a 0.1% glutaraldehyde composition for a period of 15 minutes and had been immersed in an alcohol composition comprising 95.5% ethanol for a period of 24.1 hours.

Zero headspace extraction was performed with double deionized water as the vehicle extractant. Extraction vessels were tumbled during the entire extraction process. For production lot #2, one test article was extracted with a weight of 0.051 g and fluid amount of 100 ml. The starting extraction temperature was 22° C. and the ending extraction temperature was 23° C. The extraction lasted twenty-four hours.

All sample extract solutions were observed to be clear and free of particulates. At the end of the extraction period, all test articles were observed to be intact with no observable degradation. Extracts were maintained at room temperature and were not filtered prior to analysis. The vehicle solution was analyzed by gas chromatography for glutaraldehyde determination. Control blanks contained no compounds of interest at the reported detection limits. Low level calibration standards were analyzed at the detection levels, and standard percent recoveries were within acceptable method limits. No analytical interferences were observed. All instrument calibration results were within method requirements through all portions of the analysis.

No glutaraldehyde was detected at the reported detection limit (1.0 mg/L) for production lot #2.

Two representative samples of final product (2 cm×6 cm each) from production lot #3 included amniotic membranes that had been treated with a 0.1% glutaraldehyde composition for a period of 15 minutes and had been immersed in an alcohol composition comprising 95.5% ethanol for a period of 41.3 hours.

Zero headspace extraction was performed with double deionized water as the vehicle extractant. Extraction vessels were tumbled during the entire extraction process. For production lot #3, the two samples were pooled, and a test article was extracted with a weight of 0.069 g and a fluid amount of 100 ml. The starting extraction temperature was 22° C. and the ending extraction temperature was 23° C. The extraction lasted twenty-four hours.

All sample extract solutions were observed to be clear and free of particulates. At the end of the extraction period, all test articles were observed to be intact with no observable degradation. Extracts were maintained at room temperature and were not filtered prior to analysis. The vehicle solution was analyzed by gas chromatography for glutaraldehyde determination. Control blanks contained no compounds of interest at the reported detection limits. Low level calibration standards were analyzed at the detection levels, and standard percent recoveries were within acceptable method limits. No analytical interferences were observed. All instrument calibration results were within method requirements through all portions of the analysis.

No glutaraldehyde was detected at the reported detection limit (1.0 mg/L) for production lot #3.

One sample of final product (4 cm×4 cm) from production lot #4 included an amniotic membrane that had been treated with a 0.1% glutaraldehyde composition for a period of 15 minutes and had been immersed in an alcohol composition comprising 95.5% ethanol for a period of 114.7 hours.

Zero headspace extraction was performed with double deionized water as the vehicle extractant. Extraction vessels were tumbled during the entire extraction process. For production lot #4, one test article was extracted with a weight of 0.037 g and fluid amount of 100 ml. The starting extraction temperature was 22° C. and the ending extraction temperature was 23° C. The extraction lasted twenty-four hours.

All sample extract solutions were observed to be clear and free of particulates. At the end of the extraction period, all test articles were observed to be intact with no observable degradation. Extracts were maintained at room temperature and were not filtered prior to analysis. The vehicle solution was analyzed by gas chromatography for glutaraldehyde determination. Control blanks contained no compounds of interest at the reported detection limits. Low level calibration standards were analyzed at the detection levels, and standard percent recoveries were within acceptable method limits. No analytical interferences were observed. All instrument calibration results were within method requirements through all portions of the analysis.

No glutaraldehyde was detected at the reported detection limit (1.0 mg/L) for production lot #4.

Samples from the same four production lots #1, #2, #3 and #4 were tested for residual ethanol by gas chromatography, analytical method EPA 8260B, CAS No. 64-17-5, as follows:

Three representative samples of final product (2 cm×2 cm each) from production lot #1 included amniotic membranes that had been treated with a 0.1% glutaraldehyde composition for a period of 15 minutes and had been immersed in an alcohol composition comprising 95.5% ethanol for a period of 24 hours.

Zero headspace extraction was performed with double deionized water as the vehicle extractant. Extraction vessels were tumbled during the entire extraction process. For production lot #1, the three samples were pooled, and a test article was extracted with a weight of 0.05 g and fluid amount of 100 ml. The starting extraction temperature was 22° C. and the ending extraction temperature was 23° C. The extraction lasted twenty-four hours.

All sample extract solutions were observed to be clear and free of particulates. At the end of the extraction period, all test articles were observed to be intact with no observable degradation. Extracts were maintained at room temperature and were not filtered prior to analysis. The vehicle solution was introduced into a purge and trap unit suitable for gas chromatography-mass spectrometry analysis. Control blanks contained no compounds of interest at the reported detection limits. Low level calibration standards were analyzed at the detection levels, and standard percent recoveries were within acceptable method limits. No analytical interferences were observed. All instrument calibration results were within method requirements through all portions of the analysis.

No ethanol was detected at the reported detection limit (0.5 mg/L) for production lot #1.

One sample of final product (4 cm×4 cm) from production lot #2 included an amniotic membrane that had been treated with a 0.1% glutaraldehyde composition for a period of 15 minutes and had been immersed in an alcohol composition comprising 95.5% ethanol for a period of 24.1 hours.

Zero headspace extraction was performed with double deionized water as the vehicle extractant. Extraction vessels were tumbled during the entire extraction process. For production lot #2, one test article was extracted with a weight of 0.04 g and fluid amount of 50 ml. The starting extraction temperature was 22° C. and the ending extraction temperature was 23° C. The extraction lasted twenty-four hours.

All sample extract solutions were observed to be clear and free of particulates. At the end of the extraction period, all test articles were observed to be intact with no observable degradation. Extracts were maintained at room temperature and were not filtered prior to analysis. The vehicle solution was introduced into a purge and trap unit suitable for gas chromatography-mass spectrometry analysis. Control blanks contained no compounds of interest at the reported detection limits. Low level calibration standards were analyzed at the detection levels, and standard percent recoveries were within acceptable method limits. No analytical interferences were observed. All instrument calibration results were within method requirements through all portions of the analysis.

No ethanol was detected at the reported detection limit (0.5 mg/L) for production lot #2.

Two samples of final product (4 cm×4 cm and 2 cm×6 cm) from production lot #3 included amniotic membranes that had been treated with a 0.1% glutaraldehyde composition for a period of 15 minutes and had been immersed in an alcohol composition comprising 95.5% ethanol for a period of 41.3 hours.

Zero headspace extraction was performed with double deionized water as the vehicle extractant. Extraction vessels were tumbled during the entire extraction process. For production lot #3, the two samples were pooled, and a test article was extracted with a weight of 0.08 g and fluid amount of 50 ml. The starting extraction temperature was 22° C. and the ending extraction temperature was 23° C. The extraction lasted twenty-four hours.

All sample extract solutions were observed to be clear and free of particulates. At the end of the extraction period, all test articles were observed to be intact with no observable degradation. Extracts were maintained at room temperature and were not filtered prior to analysis. The vehicle solution was introduced into a purge and trap unit suitable for gas chromatography-mass spectrometry analysis. Control blanks contained no compounds of interest at the reported detection limits. Low level calibration standards were analyzed at the detection levels, and standard percent recoveries were within acceptable method limits. No analytical interferences were observed. All instrument calibration results were within method requirements through all portions of the analysis.

No ethanol was detected at the reported detection limit (0.5 mg/L) for production lot #3.

Two samples of final product (4 cm×4 cm each) from production lot #4 included amniotic membranes that had been treated with a 0.1% glutaraldehyde composition for a period of 15 minutes and had been immersed in an alcohol composition comprising 95.5% ethanol for a period of 114.7 hours.

Zero headspace extraction was performed with double deionized water as the vehicle extractant. Extraction vessels were tumbled during the entire extraction process. For production lot #4, the two samples were pooled, and a test article was extracted with a weight of 0.09 g and fluid amount of 50 ml. The starting extraction temperature was 22° C. and the ending extraction temperature was 23° C. The extraction lasted twenty-four hours.

All sample extract solutions were observed to be clear and free of particulates. At the end of the extraction period, all test articles were observed to be intact with no observable degradation. Extracts were maintained at room temperature and were not filtered prior to analysis. The vehicle solution was introduced into a purge and trap unit suitable for gas chromatography-mass spectrometry analysis. Control blanks contained no compounds of interest at the reported detection limits. Low level calibration standards were analyzed at the detection levels, and standard percent recoveries were within acceptable method limits. No analytical interferences were observed. All instrument calibration results were within method requirements through all portions of the analysis.

No ethanol was detected at the reported detection limit (0.5 mg/L) for production lot #4.

TABLE 1

Glutaraldehyde Determination for Production Lots #1, #2, #3 and #4

| Production Lot | Total Time in Glutaraldehyde | Weight of Sample | Volume of Fluid | Starting Extraction Temperature | Ending Extraction Temperature | Duration of Extraction | Sample Results |
|---|---|---|---|---|---|---|---|
| 1 | 15 Minutes | 0.046 g | 100 mL | 22° C. | 23° C. | 24 Hours | ND* |
| 2 | 15 Minutes | 0.051 g | 100 mL | 22° C. | 23° C. | 24 Hours | ND* |
| 3 | 15 Minutes | 0.069 g | 100 mL | 22° C. | 23° C. | 24 Hours | ND* |
| 4 | 15 Minutes | 0.037 g | 100 mL | 22° C. | 23° C. | 24 Hours | ND* |

*ND = Not Detected at the Minimum Reporting Limit (1.0 mg/L)

TABLE 2

Ethanol Determination for Production Lots #1, #2, #3 and #4

| Production Lot | Total Time in Ethanol | Weight of Sample | Volume of Fluid | Starting Extraction Temperature | Ending Extraction Temperature | Duration of Extraction | Sample Results |
|---|---|---|---|---|---|---|---|
| 1 | 24.0 Hours | 0.05 g | 50 mL | 22° C. | 23° C. | 24 Hours | ND* |
| 2 | 24.1 Hours | 0.04 g | 50 mL | 22° C. | 23° C. | 24 Hours | ND* |
| 3 | 41.3 Hours | 0.08 g | 50 mL | 22° C. | 23° C. | 24 Hours | ND* |
| 4 | 114.7 Hours | 0.09 g | 50 mL | 22° C. | 23° C. | 24 Hours | ND* |

*ND = Not Detected at the Minimum Reporting Limit (0.5 mg/L)

EXAMPLE 2

Three representative samples of final product for each of three production lots manufactured according to the methods of FIG. 1 were tested for residual ethanol by gas chromatography, analytical method EPA 8260B, CAS No. 64-17-5. Samples were sent to Nelson Laboratories, Inc., 6280 South Redwood Road Salt Lake City, Utah 84123, a GLP qualified microbiology laboratory registered with the FDA and third-party accredited to ISO 17025 standards.

The three samples submitted for testing from production lot #5 (2 cm×3 cm; 2 cm×3 cm; and 1.5 cm×2 cm) included amniotic membranes that had been immersed in an alcohol composition comprising 95.5% ethanol for a period of 110 hours. The three samples submitted for testing from production lot #6 (2 cm×3 cm each) included amniotic membranes that had been immersed in an alcohol composition comprising 95.5% ethanol for a period of 25.5 hours. The three samples submitted for testing from production lot #7 (2 cm×3 cm each) included amniotic membranes that had been immersed in an alcohol composition comprising 95.5% ethanol for a period of 24.9 hours.

Zero headspace extraction was performed with double deionized water as the vehicle extractant. Extraction vessels were tumbled during the entire extraction process. For each of the three production lots, the samples were pooled, and one test article was extracted with a weight of 0.05 g and fluid amount of 50 ml. The starting extraction temperature was 22° C. and the ending extraction temperature was 23° C. The extractions lasted twenty-four hours. All sample extract solutions were observed to be clear and free of particulates. At the end of the extraction period, all test articles were observed to be intact with no observable degradation. Extracts were maintained at room temperature and were not filtered prior to analysis. The vehicle solution was introduced into a purge and trap unit suitable for gas chromatography-mass spectrometry analysis. Control blanks contained no compounds of interest at the reported detection limits. Low level calibration standards were analyzed at the detection levels, and standard percent recoveries were within acceptable method limits. No analytical interferences were observed. All instrument calibration results were within method requirements through all portions of the analysis.

The certificates of analyses for production lots #5, #6 and #7 indicated no detectable amounts of ethanol at the minimum reporting limit (0.5 mg/L). The results are summarized in Table 3 below.

TABLE 3

Ethanol Determination for Production Lots #5, #6 and #7

| Production Lot | Total Time in Ethanol | Weight of Sample | Volume of Fluid | Starting Extraction Temperature | Ending Extraction Temperature | Duration of Extraction | Sample Results |
|---|---|---|---|---|---|---|---|
| 5 | 110.0 Hours | 0.05 g | 50 mL | 22° C. | 23° C. | 24 Hours | ND* |
| 6 | 25.5 Hours | 0.05 g | 50 mL | 22° C. | 23° C. | 24 Hours | ND* |
| 7 | 24.9 Hours | 0.05 g | 50 mL | 22° C. | 23° C. | 24 Hours | ND* |

*ND = Not Detected at the Minimum Reporting Limit (0.5 mg/L)

I claim:

1. A method of preventing graft rejection in a recipient of a transplanted solid organ utilizing a resorbable organ jacket, comprising the steps of:
   providing the resorbable organ jacket comprising:
   at least one amniotic membrane, or
   at least one chorionic membrane, or
   any combination thereof;
   the method comprising the step of:
   applying the resorbable organ jacket to an external surface of the solid organ so as to envelope the entire organ immediately before transplant into the recipient,
   wherein the at least one membrane is treated with at least one alcohol composition comprising from about 90% to about 100% ethanol, and
   wherein the organ jacket is fully resorbable by the organ after application.

2. The method of claim 1, wherein the solid organ is selected from the group consisting of heart, lung, liver, kidney, pancreas, intestine, endocrine gland or stomach.

3. The method of claim 1, wherein the resorbable organ jacket includes a surface defining at least one opening for the solid organ's vasculature.

4. A method of reducing the incidence of acute or chronic rejection episodes in a recipient following a solid organ transplant utilizing a resorbable organ jacket, comprising the steps of:
   providing the resorbable organ jacket comprising:
   at least one amniotic membrane, or
   at least one chorionic membrane, or
   any combination thereof;
   the method comprising the step of:
   applying the resorbable organ jacket to an external surface of the solid organ so as to envelope the entire organ immediately before transplant into the recipient,
   wherein the at least one membrane is treated with at least one alcohol composition comprising from about 90% to about 100% ethanol, and
   wherein the organ jacket is fully resorbable by the organ after application.

5. The method of claim 4, wherein the solid organ is selected from the group consisting of heart, lung, liver, kidney, pancreas, intestine, endocrine gland or stomach.

6. The method of claim 4, wherein the resorbable organ jacket includes a surface defining at least one opening for the solid organ's vasculature.

* * * * *